United States Patent
Vuligonda et al.

(10) Patent No.: US 9,090,624 B2
(45) Date of Patent: Jul. 28, 2015

(54) AROMATIC BYCYCLIC DERIVATIVES AS CXCR4 RECEPTOR MODULATORS

(75) Inventors: Vidyasagar Vuligonda, Irvine, CA (US); Richard L. Beard, Newport Beach, CA (US); Thong Vu, Garden Grove, CA (US); John E. Donello, Dana Point, CA (US); Gerard Rodrigues, Laguna Niguel, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 286 days.

(21) Appl. No.: 13/565,478

(22) Filed: Aug. 2, 2012

(65) Prior Publication Data

US 2013/0035347 A1    Feb. 7, 2013

Related U.S. Application Data

(60) Provisional application No. 61/515,108, filed on Aug. 4, 2011.

(51) Int. Cl.
| | | |
|---|---|---|
| *C07D 495/04* | (2006.01) | |
| *A61K 31/517* | (2006.01) | |
| *A61K 31/519* | (2006.01) | |
| *C07D 401/12* | (2006.01) | |

(52) U.S. Cl.
CPC ............ *C07D 495/04* (2013.01); *C07D 401/12* (2013.01)

(58) Field of Classification Search
USPC .............................. 544/250; 514/258.1, 260.1
See application file for complete search history.

(56) References Cited

U.S. PATENT DOCUMENTS

2012/0122846 A1*   5/2012   Calderwood et al. ..... 514/212.07

FOREIGN PATENT DOCUMENTS

| EP | 2003131 | 12/2008 |
|---|---|---|
| WO | 2004-071460 | 8/2004 |
| WO | 2006-111549 | 10/2006 |
| WO | 2009-143058 | 11/2009 |

OTHER PUBLICATIONS

Crane, Isabel et al, CXCR4 Receptor Expression on Human Retinal Pigment Epithelial Cells From the Blood-Retina Barrier Leads to Chemokine Secretion and Migration in Response to Stromal Cell-Derived Factor 1a1, Journal of Immunology, 2000, 4372-4378, 165.
Cross, L.C. et al, Rules for the Nomenclature of Organic Chemistry, Section E: Stereochemistry, Pure & Appl. Chem., 1976, 11-30, 45.
Stahl, Heinrich et al, Handbook of Pharmaceutical Salts, Verlag Helvetica Chimica Acta—Zurich, 2002, 329-345.
Patent Cooperation Treaty, Notification of Transmittal of the International Search Report and the Written Opinion of the International Searching Authority, or the Declaration, Form PCT/ISA/220, Int. App. No. PCT/US2012/049362, Nov. 19, 2012.

* cited by examiner

*Primary Examiner* — Barbara P Badio
*Assistant Examiner* — Sara E Townsley
(74) *Attorney, Agent, or Firm* — Jonathan Y. Bass

(57) ABSTRACT

The present invention relates to novel aromatic bicyclic derivatives, processes for preparing them, pharmaceutical compositions containing them and their use as pharmaceuticals as modulators of the CXCR4 receptor.

6 Claims, No Drawings

AROMATIC BYCYCLIC DERIVATIVES AS CXCR4 RECEPTOR MODULATORS

CROSS-REFERENCE TO RELATED APPLICATION

This application is based, and claims priority under 35 U.S.C. §120 to U.S. Provisional Patent Application No. 61/515,108 filed on Aug. 4, 2011, and which is incorporated herein by reference.

FIELD OF THE INVENTION

The present invention relates to novel aromatic bicyclic derivatives, processes for preparing them, pharmaceutical compositions containing them and their use as pharmaceuticals as modulators of the CXCR4 receptor. The invention relates specifically to the use of these compounds and their pharmaceutical compositions to treat disorders associated with the CXCR4 receptor modulation.

BACKGROUND OF THE INVENTION

Retinal pigment epithelial (RPE) cells form part of the blood-retina barrier and have recently been shown to produce various chemokines in response to proinflammatory cytokines. RT-PCR analysis indicated that the predominant receptor expressed on RPE cells was CXCR4. The level of CXCR4 mRNA expression, but not cell surface expression, increased on stimulation with IL-1β or TNF-α. CXCR4 protein could be detected on the surface of 16% of the RPE cells using flow cytometry. (The Journal of Immunology, 2000, 165: 4372-4378.)

SUMMARY OF THE INVENTION

We have now discovered a group of novel compounds which are potent and selective CXCR4 modulators. As such, the compounds described herein are useful in treating a wide variety of disorders associated with modulation of the CXCR4 receptor. The term "modulator" as used herein, includes but is not limited to: receptor agonist, antagonist, inverse agonist, inverse antagonist, partial agonist, partial antagonist.

This invention describes compounds of Formula I, which have CXCR4 receptor biological activity. The compounds in accordance with the present invention are thus of use in medicine, for example in the treatment of humans with diseases and conditions that are alleviated by CXCR4 modulation.

In one aspect, the invention provides a compound having Formula I or the geometrical isomers, enantiomers, diastereoisomers, tautomers, zwitterions and pharmaceutically acceptable salts thereof:

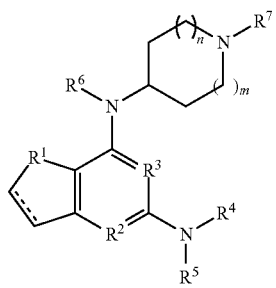

Formula I wherein:
" ----- " is a

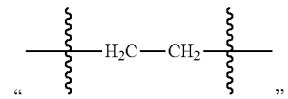

bond or a

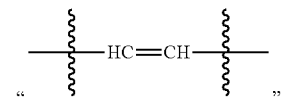

bond;
n is 0 or 1;
m is 0, 1 or 2;
$R^1$ is S, O, $CR^8R^9$ or $NR^{10}$;
$R^2$ is CH or N;
$R^3$ is CH or N;
$R^4$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl, substituted or unsubstituted heterocycle or substituted or unsubstituted aryl;
$R^5$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted aryl;
$R^6$ is H, substituted or unsubstituted —$C_{1-6}$ alkyl, substituted or unsubstituted —$C_{2-6}$ alkenyl, or substituted or unsubstituted —$C_{2-6}$ alkynyl;
$R^7$ is substituted or unsubstituted $C_{1-6}$ alkyl, substituted or unsubstituted $C_{3-8}$ cycloalkyl, substituted or unsubstituted $C_{3-8}$ cycloalkenyl, substituted or unsubstituted heterocycle, substituted or unsubstituted aryl, substituted or unsubstituted benzyl or $CH_2$ (substituted or unsubstituted heterocycle);
$R^8$ is H or substituted or unsubstituted —$C_{1-6}$ alkyl;
$R^9$ is H or substituted or unsubstituted —$C_{1-6}$ alkyl; and
$R^{10}$ is H or substituted or unsubstituted —$C_{1-6}$ alkyl.

In one aspect, the invention provides a compound having Formula I wherein:
" ----- " is a

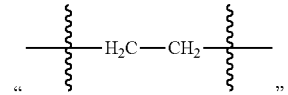

bond;
n is 1;
m is 1;
$R^1$ is S, O, $CR^8R^9$ or $NR^{10}$;
$R^2$ is CH or N;
$R^3$ is CH or N;
$R^4$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl heterocycle or substituted or unsubstituted aryl;

$R^5$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted aryl;
$R^6$ is H, substituted or unsubstituted —$C_{1-6}$ alkyl, substituted or unsubstituted —$C_{2-6}$ alkenyl, or substituted or unsubstituted —$C_{2-6}$ alkynyl;
$R^7$ is substituted or unsubstituted $C_{1-6}$ alkyl, substituted or unsubstituted $C_{3-8}$ cycloalkyl, substituted or unsubstituted $C_{3-8}$ cycloalkenyl, substituted or unsubstituted heterocycle, substituted or unsubstituted aryl, substituted or unsubstituted benzyl or $CH_2$ (substituted or unsubstituted heterocycle);
$R^8$ is H or substituted or unsubstituted —$C_{1-6}$ alkyl;
$R^9$ is H or substituted or unsubstituted —$C_{1-6}$ alkyl; and
$R^{10}$ is H or substituted or unsubstituted —$C_{1-6}$ alkyl.

In one aspect, the invention provides a compound having Formula I wherein:
" ----- " is a

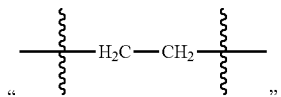

bond;
n is 1;
m is 1;
$R^1$ is $CR^8R^9$;
$R^2$ is N;
$R^3$ is N;
$R^4$ is H;
$R^5$ is substituted or unsubstituted —$C_{1-6}$ alkyl;
$R^6$ is H;
$R^7$ is substituted or unsubstituted $C_{1-6}$ alkyl, or substituted or unsubstituted benzyl;
$R^8$ is H; and
$R^9$ is H.

In one aspect, the invention provides a compound having Formula I wherein:
" ----- " is a

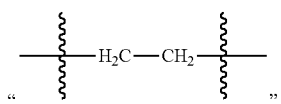

bond;
n is 1;
m is 1;
$R^1$ is $CR^8R^9$;
$R^2$ is N;
$R^3$ is N;
$R^4$ is H;
$R^5$ is substituted or unsubstituted —$C_{1-6}$ alkyl;
$R^6$ is H;
$R^7$ is substituted $C_{1-6}$ alkyl with a substituted or unsubstituted phenyl;
$R^8$ is H; and
$R^9$ is H.

In one aspect, the invention provides a compound having Formula I wherein:
" ----- " is a

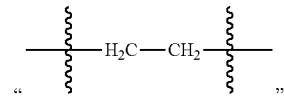

bond;
n is 1;
m is 1;
$R^1$ is $CR^8R^9$;
$R^2$ is N;
$R^3$ is N;
$R^4$ is H;
$R^5$ is substituted —$C_{1-6}$ alkyl with an amine group;
$R^6$ is H;
$R^7$ is substituted $C_{1-6}$ alkyl with a substituted phenyl;
$R^8$ is H; and
$R^9$ is H.

In one aspect, the invention provides a compound having Formula I wherein:
" ----- " is a

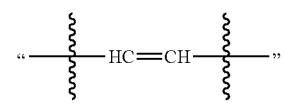 [SMILES: *C=C*]

bond;
n is 1;
m is 1;
$R^1$ is S, O, $CR^8R^9$ or $NR^{10}$;
$R^2$ is CH or N;
$R^3$ is CH or N;
$R^4$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl heterocycle or substituted or unsubstituted aryl;
$R^5$ is H, substituted or unsubstituted —$C_{1-6}$ alkyl, substituted or unsubstituted —$C_{2-6}$ alkenyl, substituted or unsubstituted —$C_{2-6}$ alkynyl, substituted or unsubstituted $C_{3-8}$ cycloalkyl, substituted or unsubstituted $C_{3-8}$ cycloalkenyl substituted or unsubstituted heterocycle or substituted or unsubstituted aryl;
$R^6$ is H, substituted or unsubstituted —$C_{1-6}$ alkyl, substituted or unsubstituted —$C_{2-6}$ alkenyl, or substituted or unsubstituted —$C_{2-6}$ alkynyl;
$R^7$ is substituted or unsubstituted $C_{1-6}$ alkyl, substituted or unsubstituted $C_{3-8}$ cycloalkyl, substituted or unsubstituted $C_{3-8}$ cycloalkenyl, substituted or unsubstituted heterocycle, substituted or unsubstituted aryl, substituted or unsubstituted benzyl or $CH_2$ (substituted or unsubstituted heterocycle);
$R^8$ is H or substituted or unsubstituted —$C_{1-6}$ alkyl;
$R^9$ is H or substituted or unsubstituted —$C_{1-6}$ alkyl; and
$R^{10}$ is H or substituted or unsubstituted —$C_{1-6}$ alkyl.

In one aspect, the invention provides a compound having Formula I wherein:
" ----- " is a

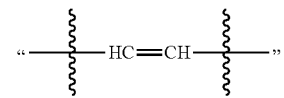 [SMILES: *C=C*]

bond;
n is 1;
m is 1;

$R^1$ is S;
$R^2$ is N;
$R^3$ is N;
$R^4$ is H;
$R^5$ is substituted or unsubstituted —$C_{1-6}$ alkyl;
$R^6$ is H; and
$R^7$ is substituted or unsubstituted $C_{1-6}$ alkyl, or substituted or unsubstituted benzyl.

In one aspect, the invention provides a compound having Formula I wherein:
" ----- " is a

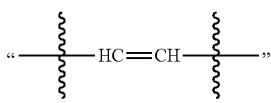 [SMILES: *C=C*]

bond;
n is 1;
m is 1;
$R^1$ is S;
$R^2$ is N;
$R^3$ is N;
$R^4$ is H;
$R^5$ is substituted —$C_{1-6}$ alkyl with an amine group;
$R^6$ is H; and
$R^7$ is substituted $C_{1-6}$ alkyl with a substituted phenyl.

In one aspect, the invention provides a compound having Formula I wherein:
" ----- " is a

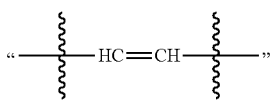 [SMILES: *C=C*]

bond;
n is 1;
m is 1;
$R^1$ is S or $CH_2$;
$R^2$ is N;
$R^3$ is N;
$R^4$ is H;
$R^5$ is

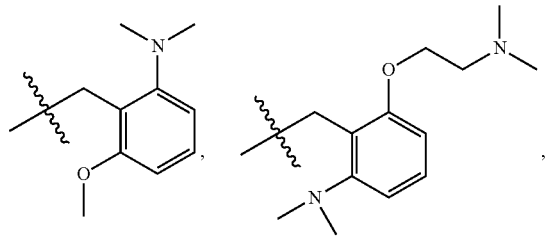

$R^6$ is H;
$R^7$ is

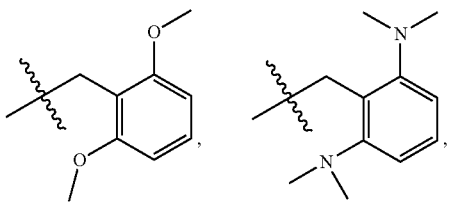

-continued

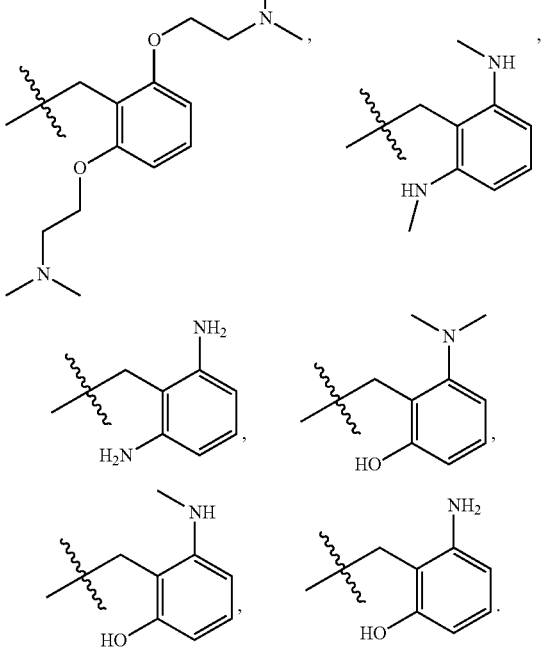

In one aspect, the invention provides a compound having Formula I wherein:
" ----- " is a

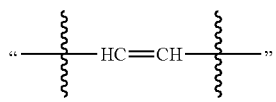 [SMILES: *C=C*]

bond;
n is 1;
m is 1;
$R^1$ is S;
$R^2$ is N;
$R^3$ is N;
$R^4$ is H;
$R^5$ is

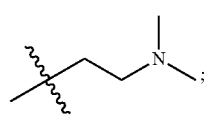 [SMILES: *CCN(C)C]

$R^6$ is H;

$R^7$ is

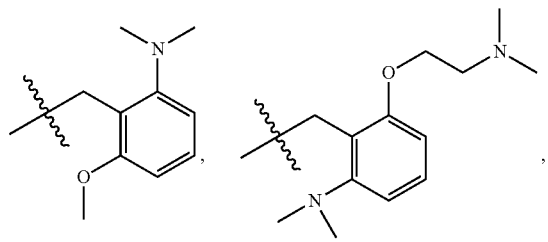

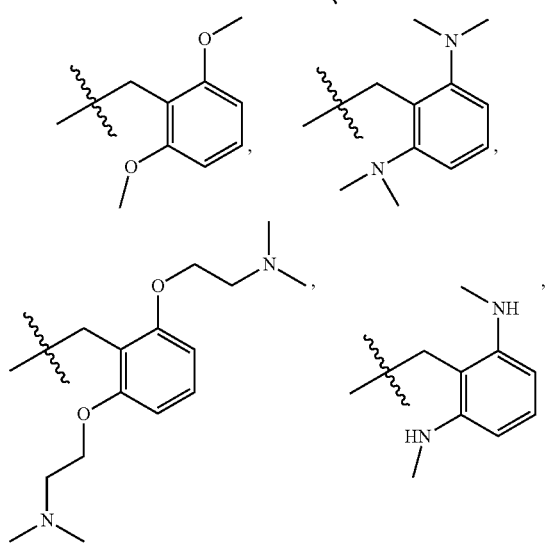

In one aspect, the invention provides a compound having Formula I wherein:

" ----- " is a

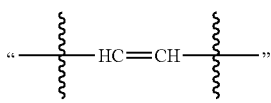 [SMILES: *C=C*]

bond;
n is 1;
m is 1;
$R^1$ is S;
$R^2$ is N;
$R^3$ is N;
$R^4$ is H;

$R^5$ is

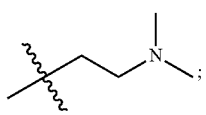 [SMILES: *CCN(C)C]

$R^6$ is H;
$R^7$ is

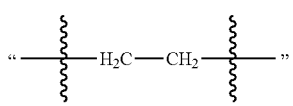 [SMILES: *CC*]

In one aspect, the invention provides a compound having Formula I wherein:

" ----- " is a $$\text{"} -\!\!\!-\!\!\!- H_2C-CH_2 -\!\!\!-\!\!\!- \text{"}$$

bond
n is 1;
m is 1;
$R^1$ is S or $CH_2$;
$R^2$ is N;
$R^3$ is N;
$R^4$ is H;
$R^5$ is

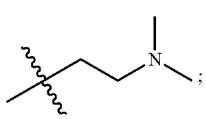

$R^6$ is H;
$R^7$ is

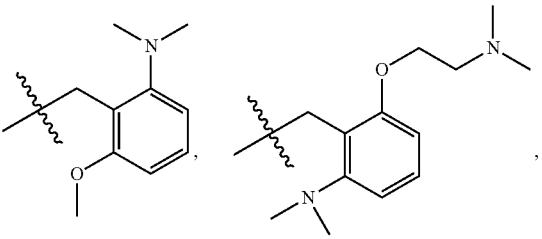

-continued
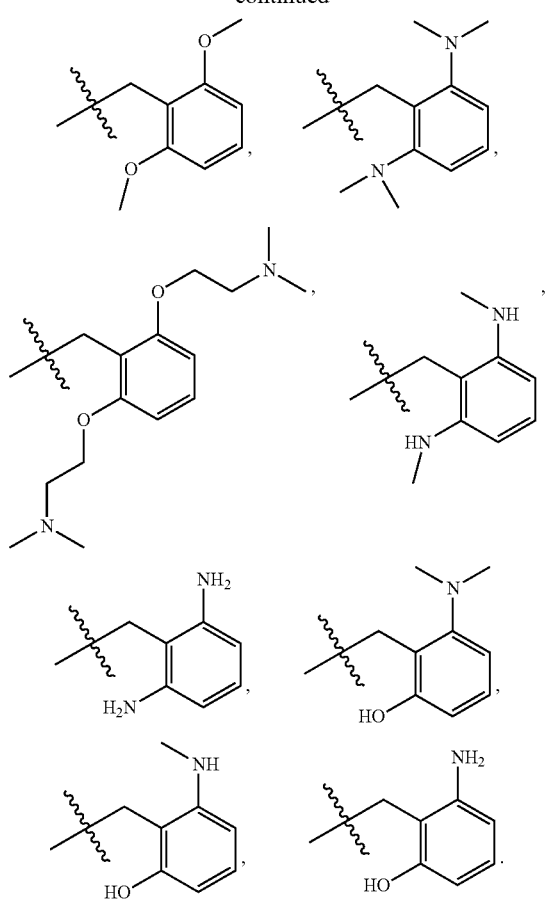
In one aspect, the invention provides a compound having Formula I wherein:
" ----- " is a
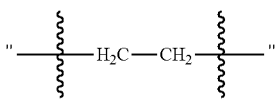
bond;
n is 1;
m is 1;
$R^1$ is $CH_2$;
$R^2$ is N;
$R^3$ is N;
$R^4$ is H;
$R^5$ is
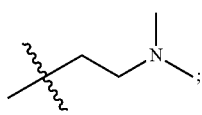 [SMILES: *CCN(C)C]
$R^6$ is H;
$R^7$ is
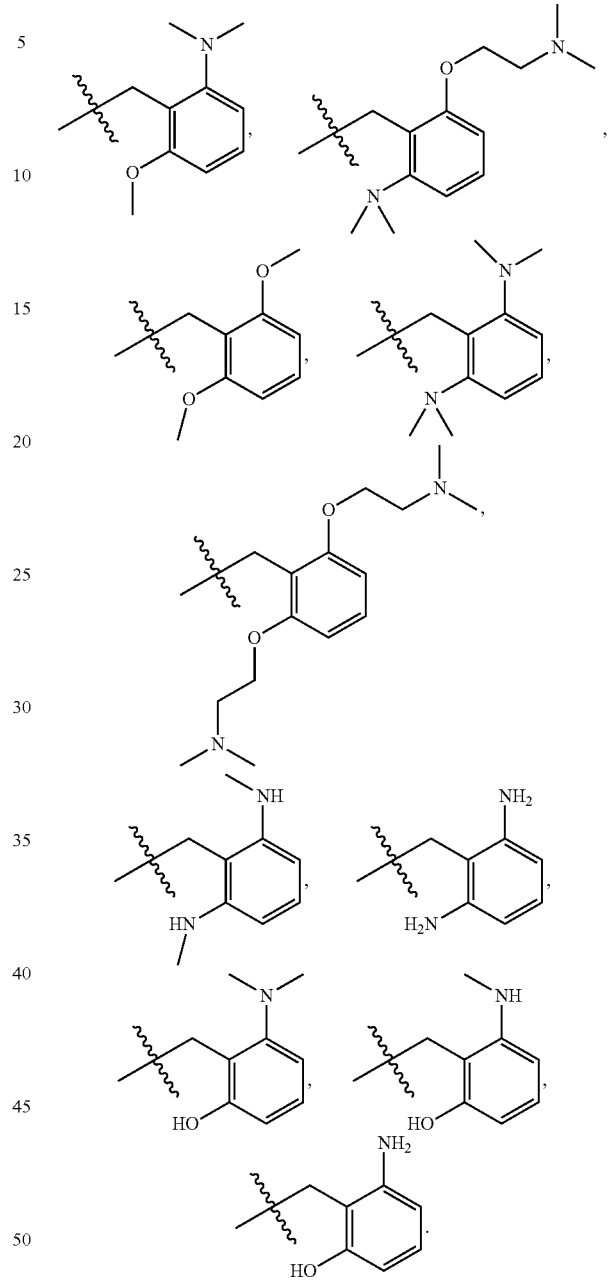
In one aspect, the invention provides a compound having Formula I wherein:
" ----- " is a
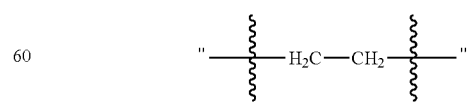
bond;
n is 1;
m is 1;
$R^1$ is $CH_2$;

$R^2$ is N;
$R^3$ is N;
$R^4$ is H;
$R^5$ is

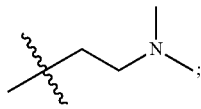 [SMILES: *CCN(C)C]

$R^6$ is H;
$R^7$ is

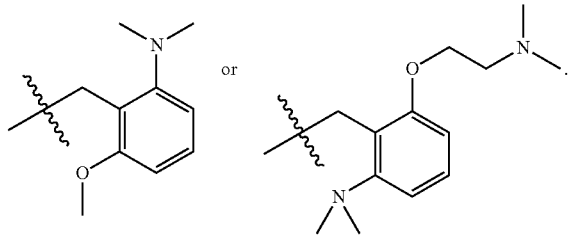 [SMILES: *Cc1c(OC)cccc1N(C)C ; *Cc1c(OCCN(C)C)cccc1N(C)C]

In one aspect, the invention provides a compound having Formula I wherein:
"------" is a

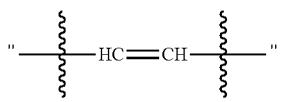 [SMILES: *C=C*]

bond or a

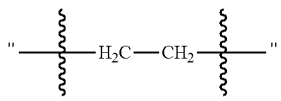

bond;
n is 1;
m is 1;
$R^1$ is S or $CR^8R^9$;
$R^2$ is N;
$R^3$ is N;
$R^4$ is H;
$R^5$ is

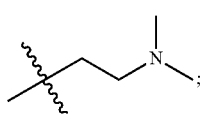 [SMILES: *CCN(C)C]

$R^6$ is H;
$R^7$ is

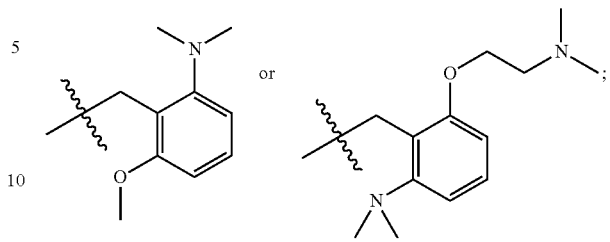

$R^8$ is H; and
$R^9$ is H.

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can be independently substituted by halogen, hydroxyl, cycloalkyl, amine groups, heterocyclic groups, carboxylic acid groups, phosphonic acid groups, sulphonic acid groups, phosphoric acid groups, nitro groups, amide groups, sulfonamides groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen, hydroxyl, cycloalkyl, amine, heterocyclic groups, carboxylic acid groups, phosphonic acid groups, sulphonic acid groups, phosphoric acid groups, nitro groups, amide groups, sulfonamides groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen, hydroxyl, cycloalkyl, amine, heterocyclic groups, carboxylic acid groups, phosphonic acid groups, sulphonic acid groups, phosphoric acid groups, nitro groups, amide groups, sulfonamides groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by $C_{1-6}$ alkyl, as defined above, or by halogen.

The term "alkynyl", as used herein, refers to a monovalent or divalent hydrocarbon radical having 2 to 6 carbon atoms, derived from a saturated alkyl, having at least one triple bond. Alkynyl groups can be substituted by $C_{1-6}$ alkyl, as defined above, or by halogen.

The term "heterocycle" as used herein, refers to a 3 to 10 membered ring, which can be aromatic or non-aromatic, saturated or unsaturated, containing at least one heteroatom selected form O or N or S or combinations of at least two thereof, interrupting the carbocyclic ring structure. The heterocyclic ring can be saturated or unsaturated. The heterocyclic ring can be interrupted by a C=O; the S and N heteroatoms can be oxidized. Heterocycles can be monocyclic or polycyclic. Heterocyclic ring moieties can be substituted by halogen, hydroxyl, cycloalkyl, heterocyclic groups, carboxylic acid groups, phosphonic acid groups, sulphonic acid groups, phosphoric acid groups, nitro groups, amide groups, sulfonamides groups, amine groups, —O($C_{1-6}$ alky) groups, or —O($C_{1-6}$ alky) groups wherein the alkyl group can be substituted as defined above especially by amine groups.

The term "aryl" as used herein, refers to an organic moiety derived from an aromatic hydrocarbon consisting of a ring containing 6 to 10 carbon atoms by removal of one hydrogen, which can be substituted by halogen, hydroxyl, cycloalkyl, amine groups, —O($C_{1-6}$ alky) groups, heterocyclic groups, carboxylic acid groups, phosphonic acid groups, sulphonic acid groups, phosphoric acid groups, nitro groups, amide groups, sulfonamides groups. Usually aryl is phenyl. Preferred substitution site on the aryl ring is the ortho position.

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "sulfonyl" as used herein, represents a group of formula "—$SO_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "ketone" as used herein, represents an organic compound having a carbonyl group linked to a carbon atom such as —(CO)$R^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "nitro" as used herein, represents a group of formula "—$NO_2$".

The term "cyano" as used herein, represents a group of formula "—CN".

The term "amide" as used herein, represents a group of formula "—C(O)$NR^xR^y$," wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2NR^xR^y$" wherein $R^x$ and $R^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Preferred compounds of the invention are:
$N^2$-[2-(dimethylamino)ethyl]-$N^4$-{1-[2-(dimethylamino)-6-methoxybenzyl]piperidin-4-yl}-6,7-dihydro-5H-cyclopenta[d]pyrimidine-2,4-diamine;
$N^4$-(1-(2-(Dimethylamino)-6-(2-dimethylamino)ethoxy)benzyl)piperidin-4-yl)-$N^2$-(2-(dimethylamino)ethyl) thieno[3,2-d]pyrimidine-2,4-diamine.

Some compounds of Formula I and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal& Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention. The compounds of the invention are indicated for use in treating or preventing conditions in which there is likely to be a component involving the CXCR4 receptor.

In another embodiment, there are provided pharmaceutical compositions including at least one compound of the invention in a pharmaceutically acceptable carrier.

In a further embodiment of the invention, there are provided methods for treating disorders associated with modulation of the CXCR4 receptor.

Such methods can be performed, for example, by administering to a subject in need thereof a pharmaceutical composition containing a therapeutically effective amount of at least one compound of the invention.

The compounds of the invention are useful for the treatment of mammals, including humans, with a range of conditions and diseases that are alleviated by the CXCR4 modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the retinal pigment epithelial; inflammatory and autoimmune diseases including, but not limited to rheumatoid arthritis, multiple sclerosis, inflammatory bowel disease (ulcerative colitis and Crohn's), lupus erythematosus, asthma, chronic obstructive pulmonary disease (COPD), diabetes mellitus, atherosclerosis, psoriasis, spondyloarthopathies (ankylosing spondylitis), sjogrens syndrome, osteoarthritis, allergy, chronic graft rejection, graft vs. host disease, thyroiditis, Goodpasture's syndrome, scleroderma; oncology related: metastasis, angiogenesis, stem cell mobilization.

In still another embodiment of the invention, there are provided methods for treating disorders associated with modulation of the CXCR4 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the retinal pigment epithelial; inflammatory and autoimmune diseases including, but not limited to rheumatoid arthritis, multiple sclerosis, inflammatory bowel disease (ulcerative colitis and crohn's), lupus erythematosus, asthma, chronic obstructive pulmonary disease (COPD), diabetes mellitus, atherosclerosis, psoriasis, spondyloarthopathies (ankylosing spondylitis), sjogrens syndrome, osteoarthritis, allergy, chronic graft rejection, graft vs. host disease, thyroiditis, Goodpasture's syndrome, scleroderma; oncology related: metastasis, angiogenesis, stem cell mobilization. The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the CXCR4 receptor. Thus, in further embodiments of the invention, there are provided methods for treating a disorder associated with modulation of the CXCR4 receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made. At this stage, those skilled in the art will appreciate that many additional compounds that fall under the scope of the invention may be prepared by performing various common chemical reactions. Details of certain specific chemical transformations are provided in the examples.

Scheme 1

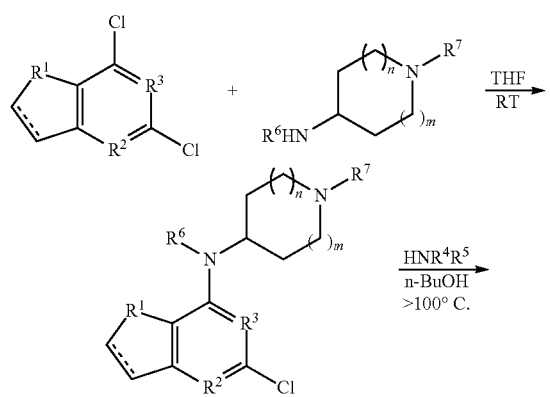

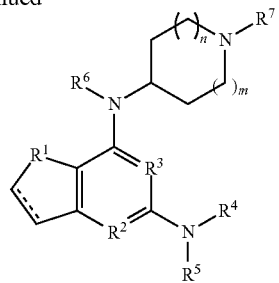

Formula I

Commercially available dichloropyrimidines were reacted with a 4-aminopiperidine in tetrahydrofuran in the presence of potassium carbonate at room temperature. After 16 hours, the reaction mixture was diluted with dichloromethane and the potassium carbonate was filtered off. The solvent was removed and the crude reaction mixture was purified by column chromatography on silicagel to give a pyrimidine-piperidine intermediate. Further the intermediate was reacted with the desired diamine compound in refluxing butanol. The compound of Formula I was isolated after column chromatography on silicagel.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8.0. In general, characterization of the compounds is performed according to the following methods:

NMR spectra are recorded on 300 and/or 600 MHz Varian and acquired at room temperature. Chemical shifts are given in ppm referenced either to internal TMS or to the solvent signal. The optical rotation was recorded on Perkin Elmer Polarimeter 341, 589 nm at 20° C., Na/Hal lamp.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

The following abbreviations are used in the examples:
CH$_2$Cl$_2$ dichloromethane
K$_2$CO$_3$ potassium carbonate
CDCl$_3$ deuterated chloroform
THF tetrahydrofuran
RT room temperature
NH$_3$ ammonia
MeOH methanol
n-BuOH butanol
CF$_3$CO$_2$H trifluoroacetic acid
TLC thin layer chromatography
CD$_3$OD deuterated methanol
NaHCO$_3$ sodium bicarbonate
NaCNBH$_3$ sodium borohydride
ZnCl$_2$ zinc chloride The following synthetic methods illustrate how compounds according to the invention can be made. Those skilled in the art will be routinely able to modify and/or adapt the following schemes to synthesize any compound of the invention covered by Formula I.

Example 1

Intermediate 1

2-Chloro-N-{1-[2-(dimethylamino)-6-methoxybenzyl]piperidin-4-yl}-6,7-dihydro-5H-cyclopenta[d]pyrimidin-4-amine

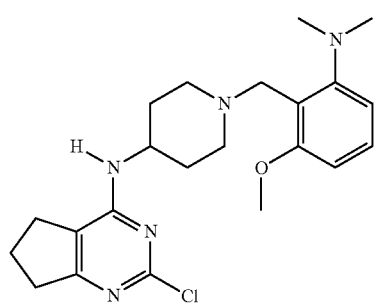 [SMILES: COc1cccc(N(C)C)c1CN1CCC(Nc2nc(Cl)nc3c2CCC3)CC1]

A mixture of dichloro pyrimidine compound 2,4-Dichloro-6,7-dihydro-5H-cyclopentapyrimidine, (CAS 5466-43-3) (188 mg, 1 mmol), amino compound 1-[[2-(dimethylamino)-6-methoxyphenyl]methyl]-4-piperidinamine 2,2,2-trifluoroacetate (CAS 1197156-28-7) (118 mg, 0.5 mmol), K$_2$CO$_3$ (720 mg, 5.2 mmol), and THF (5 mL) was stirred at RT for 16 h. The reaction mixture was diluted with CH$_2$Cl$_2$ (40 mL), and the solid K$_2$CO$_3$ was filtered off. The solvent was removed under reduced pressure and the crude product was purified by silicagel column chromatography (7N NH$_3$ in MeOH:CH$_2$Cl$_2$, 2:98) and Intermediate 1 was isolated as a pale yellow solid and was used as it is in the next step.

Example 2

Compound 1

N$^2$-[2-(Dimethylamino)ethyl]-N$^4$-{1-[2-(dimethylamino)-6-methoxybenzyl]piperidin-4-yl}-6,7-dihydro-5H-cyclopenta[d]pyrimidine-2,4-diamine

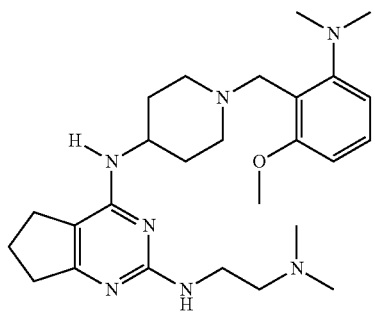 [SMILES: COc1cccc(N(C)C)c1CN1CCC(Nc2nc(NCCN(C)C)nc3c2CCC3)CC1]

A solution of Intermediate 1 (160 mg, 0.38 mmol), N1,N1-dimethyl-1,2-Ethanediamine (CAS 108-00-9) (200 mg, 2.3 mmol), and n-BuOH (3 mL) was heated to 110° C. for 72 h. The solvent was removed under reduced pressure. The crude reaction product was purified by silicagel column chromatography (7N NH$_3$ in MeOH:CH$_2$Cl$_2$, 2:98).

Compound 1 was isolated as a pale yellow solid.

$^1$HNMR (CDCl$_3$): δ 1.30-1.50 (m, 2H), 1.90-2.05 (m, 4H), 2.25-2.38 (m, 2H), 2.25 (s, 3H), 2.45-2.55 (m, 2H), 2.60-2.70 (m, 2H), 2.70 (t, J=7.8 Hz, 1H), 2.78 (s, 6H), 2.80-2.95 (m, 1H), 3.44 (q, J=5.7 Hz, 2H), 3.65 (s, 2H), 3.80 (s, 3H), 6.64 (d, J=8.4 Hz, 1H), 6.77 (d, J=8.4 Hz, 1H), 7.20 (t, J=8.4 Hz, 1H).

Example 3

Intermediate 2 tert-Butyl 4-[(2-chlorothieno[3,2-d]pyrimidin-4-yl)amino]piperidine-1-carboxylate

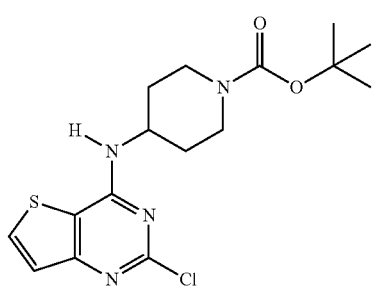 [SMILES: CC(C)(C)OC(=O)N1CCC(Nc2nc(Cl)nc3ccsc23)CC1]

A mixture of dichloro thienopyrimidine compound 2,4-dichloro-thieno[3,2-d]pyrimidine (CAS 16234-14-3) (500 mg, 2.4 mmol), amino compound 1-Piperidinecarboxylic acid, 4-amino-, 1,1-dimethylethyl ester (CAS 87120-72-7) (490 mg, 2.45 mmol), K₂CO₃ (3.4 g, 24.5 mmol), and THF (20 mL) was stirred at RT for 120 h. The solvent was removed under reduced pressure. The crude product was purified by silicagel column chromatography (7N NH₃ in MeOH:CH₂Cl₂, 2:98) and Intermediate 2 was isolated as a pale yellow solid.

Example 4

Intermediate 3 tert-Butyl 4-({2-[(3-methylbutyl)amino]thieno[3,2-d]pyrimidin-4-yl}amino)piperidine-1-carboxylate

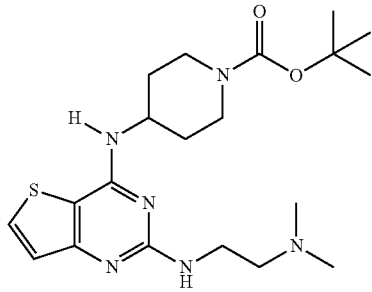 [SMILES: CN(C)CCNc1nc(NC2CCN(C(=O)OC(C)(C)C)CC2)c2sccc2n1]

Intermediate 3 was prepared from Intermediate 2 (274 mg, 0.75 mmol) and N1,N1-Dimethyl-1,2-ethanediamine (242 mg, 2.6 mmol) using the procedure described in Example 3.
¹HNMR (CDCl₃): δ 1.30-1.50 (m, 2H), 1.49 (s, 9H), 1.90-2.05 (br d, J=9 Hz, 2H), 2.34 (s, 6H), 2.61 (t, J=6.0 Hz, 2H), 2.89 (br s, 2H). 3.53 (t, J=9.0 Hz. 2H), 4.11 (br d, J=12.0 Hz, 2H), 4.31 (br s, 1H), 7.01 (d, J=6.0 Hz, 1H), 7.70 (d, J=6.0 Hz, 1H).

Example 5

Intermediate 4

N²-(3-Methylbutyl)-N⁴-piperidin-4-ylthieno[3,2-d]pyrimidine-2,4-diamine

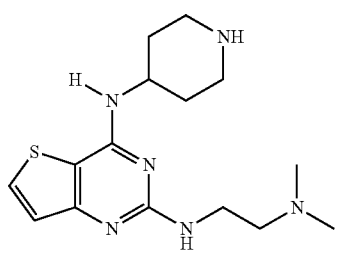 [SMILES: CN(C)CCNc1nc(NC2CCNCC2)c2sccc2n1]

A mixture of Intermediate 3 (75 mg, 0.18 mmol), CH₂Cl₂ (5 mL), CF₃CO₂H (1 mL) was stirred for 1 h at RT. The reaction was quenched with solid NaHCO₃ and filtered. The solvent was removed under reduced pressure and the crude mixture was purified by preparative TLC (7N NH₃ in MeOH:CH₂Cl₂; 1:9). Intermediate 4 was isolated as a yellow oil.

¹HNMR (CD₃OD): δ 1.54 (dq, J=3.0, 12.0 Hz, 2H), 2.02 (d, J=12.0 Hz, 2H), 2.27 (s, 6H), 2.56 (t, J=6.0 Hz, 2H), 2.67 (dt, J=3.0, 12.0 Hz, 2H), 3.08 (d, J=12.0 Hz, 2H), 3.51 (t, J=6.0 Hz, 2H), 4.20-4.28 (m, 1H), 7.00 (d, J=6.0 Hz, 1H), 7.69 (d, J=6.0 Hz, 1H).

Example 6

Compound 2

N⁴-(1-(2-(Dimethylamino)-6-(2-dimethylamino)ethoxy)benzyl)piperidin-4-yl)-N²-(2-(dimethylamino)ethyl)thieno[3,2-d]pyrimidine-2,4-diamine

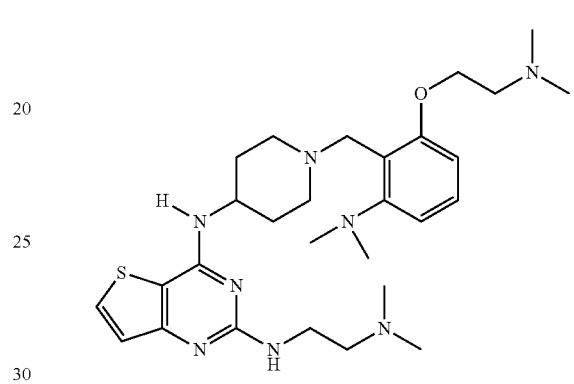

To a solution of Intermediate 4 (51 mg, 0.16 mmol), aldehyde compound 2-(dimethylamino)-6-[2-(dimethylamino)ethoxy]-benzaldehyde (CAS 1197156-43-6) (38 mg, 0.16 mmol) in MeOH (5 mL) was added NaCNBH₃ (20 mg, 0.32 mmol) and ZnCl₂ (22 mg, 0.16 mmol) in MeOH (3 mL). The reaction was stirred for 18 h at RT. The solvent was removed under reduced pressure and the crude product was purified by silicagel chromatography (7N NH₃ in MeOH:CH₂Cl₂, 1:99). Compound 2 was isolated as a yellow solid.
¹HNMR (CD₃OD): δ 1.98 (br q, J=12.0 Hz, 2H), 2.44 (s, 6H), 2.50 (s, 6H), 2.71 (s, 6H), 2.78-2.92 (m, 4H), 3.17 (t, J=12.0 Hz, 2H), 3.83 (t, J=12.0 Hz, 2H), 3.59 (t, J=9.0 Hz, 2H), 4.25 (t, J=6.0 Hz, 2H), 4.45 (s, 2H), 6.94 (d, J=9.0 Hz, 1H), 7.02 (d, J=9.0 Hz, 1H), 7.05 (d. J=6.0 Hz, 1H), 7.42 (t, J=9.0 Hz, 1H), 7.77 (d, J=6.0 Hz, 1H).

Example 7

Measurement of Intracellular $Ca^{+2}$ Responses for CXCR4 Compounds

HEK-Gqi5 cells stably expressing the human CXCR4 receptor were utilized for these studies. The growth media for the CXCR4 receptor expressing cell line was DMEM high glucose medium supplemented with 10% fetal bovine serum (FBS), 1% antibiotic-antimycotic, 50 ug/ml hygromycin B, and 400 µg/ml geneticin. Ten thousand cells per well were plated into 384-well poly-D-lysine coated plates one day prior to use. On the day of the experiment, the cells were washed twice with Hank's Balanced Salt Solution supplemented with 20 mM hepes (HBSS/hepes buffer). The cells were then dye loaded with 2 uM Fluo-4 diluted in the HBSS/Hepes buffer and incubated at 37° C. for 40 minutes. Extracellular dye was removed by washing the cell plates four times prior to placing the plates in the FLIPR (Fluorometric Imaging Plate Reader, Molecular Devices). Ligands were diluted in HBSS/Hepes buffer and prepared in 384-well microplates. The positive control, stromal-cell derived factor-1 (SDF-1α), was diluted in HBSS/Hepes buffer with 4 mg/ml fatty acid free bovine serum albumin. Two drug additions were made by the FLIPR. The first drug addition was the test drug in concentrations ranging from 2.44 nM to 40,000 nM. After this addition, fluorescent measurements were taken. Any calcium release in response to this drug addition represents agonist activity of the compounds. The second drug addition was SDF-1α at a final concentration of 1.9 nM ($EC_{65}$). Fluorescence measurements were also taken after this second drug addition and were used to determine the ability of the test compounds to antagonize the SDF-1α response. Results were expressed as $EC_{50}$ and efficacy values, as well as $IC_{50}$ and percent antagonism values. As controls, SDF-1α (CXCR4 agonist) and AMD3100 (CXCR4 antagonist) dose-response curves were also determined in each study.

TABLE 1

| Compound IUPAC name | CXCR4 $IC_{50}$ [nM] (% Inhibition) |
| --- | --- |
| $N^2$-[2-Dimethylamino)ethyl]-$N^4$-{1-[2-(dimethylamino)-6-methoxybenzyl]piperidin-4-yl}-6,7-dihydro-5H-cyclopenta[d]pyrimidine-2,4-diamine | 2924 (93) |
| $N^4$-(1-(2-(Dimethylamino)ethoxy)benzyl)piperidin-4-y1)-$N^2$-(2-(dimethylamino)ethyl)thieno[3,2-d]pyrimidine-2,4-diamine | 110 (95) |

What is claimed is:

1. A compound represented by Formula I, its enantiomers, diastereoisomers, tautomers or a pharmaceutically acceptable salt thereof,

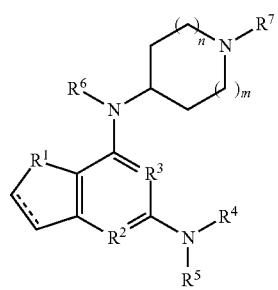

Formula I wherein:

"=====" is a

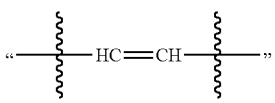

bond;

n is 1;
m is 1;
$R^1$ is S;
$R^2$ is N;
$R^3$ is N;
$R^4$ is H;
$R^5$ is

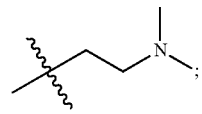

$R^6$ is H; and
$R^7$ is substituted or unsubstituted $C_{1-6}$ alkyl, or substituted or unsubstituted benzyl.

2. A compound represented by Formula I, its enantiomers, diastereoisomers, tautomers or a pharmaceutically acceptable salt thereof,

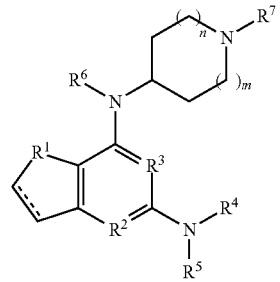

Formula I wherein:

"=====" is a

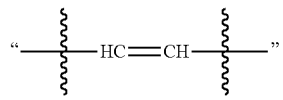

bond or a

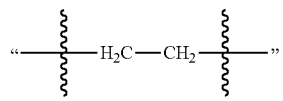

bond;

n is 1;
m is 1;
$R^1$ is S or $CR^8R^9$;
$R^2$ is N;
$R^3$ is N;
$R^4$ is H;
$R^5$ is

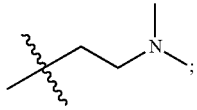

$R^6$ is H;

$R^7$ is

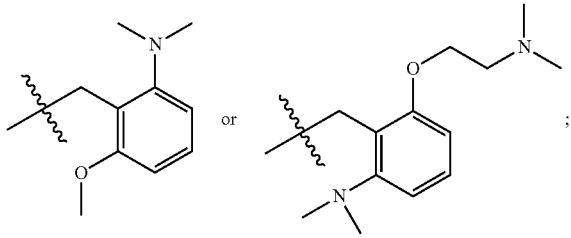 [SMILES: *Cc1c(OC)cccc1N(C)C ; *Cc1c(OCCN(C)C)cccc1N(C)C]

$R^8$ is H; and
$R^9$ is H.

3. A compound selected from:
$N^2$-[2-(dimethylamino)ethyl]-$N^4$-{1-[2-(dimethylamino)-6-methoxybenzyl]piperidin-4-yl}-6,7-dihydro-5H-cyclopenta[d]pyrimidine-2,4-diamine; and
$N^4$-(1-(2-(Dimethylamino)-6-(2-dimethylamino)ethoxy)benzyl)piperidin-4-yl)-$N^2$-(2-(dimethylamino)ethyl)thieno[3,2-d]pyrimidine-2,4-diamine.

4. A pharmaceutical composition comprising as active ingredient a therapeutically effective amount of a compound according to claim 1 and a pharmaceutically acceptable adjuvant, diluents or carrier.

5. A pharmaceutical composition comprising as active ingredient a therapeutically effective amount of a compound according to claim 2 and a pharmaceutically acceptable adjuvant, diluents or carrier.

6. A pharmaceutical composition according to claim 5 wherein the compound is selected from:
$N^2$-[2-(dimethylamino)ethyl]-$N^4$-{1-[2-(dimethylamino)-6-methoxybenzyl]piperidin-4-yl}-6,7-dihydro-5H-cyclopenta[d]pyrimidine-2,4-diamine; and
$N^4$-(1-(2-(Dimethylamino)-6-(2-dimethylamino)ethoxy)benzyl)piperidin-4-yl)-$N^2$-(2-(dimethylamino)ethyl)thieno[3,2-d]pyrimidine-2,4-diamine.

* * * * *